(12) United States Patent
Fitzsimmons

(10) Patent No.: US 7,089,060 B1
(45) Date of Patent: Aug. 8, 2006

(54) METHODS OF STIMULATING CELL RECEPTOR ACTIVITY USING ELECTROMAGNETIC FIELDS

(75) Inventor: Robert J. Fitzsimmons, Colton, CA (US)

(73) Assignee: AMEI Technologies Inc., Wilimington, DE (US)

( * ) Notice: Subject to any disclaimer, the term of this patent is extended or adjusted under 35 U.S.C. 154(b) by 496 days.

(21) Appl. No.: 10/080,642

(22) Filed: Feb. 22, 2002
(Under 37 CFR 1.47)

Related U.S. Application Data

(60) Provisional application No. 60/271,030, filed on Feb. 23, 2001.

(51) Int. Cl.
| | |
|---|---|
| *A61N 1/08* | (2006.01) |
| *A61N 1/10* | (2006.01) |
| *A61N 1/18* | (2006.01) |
| *A61N 1/20* | (2006.01) |
| *A61N 1/00* | (2006.01) |

(52) U.S. Cl. ............................ 607/50; 607/2; 607/52
(58) Field of Classification Search .................. 514/2, 514/12; 530/300, 350
See application file for complete search history.

(56) References Cited

U.S. PATENT DOCUMENTS

| 5,100,373 A | * | 3/1992 | Liboff et al. ................ 600/13 |
| 6,334,069 B1 | * | 12/2001 | George et al. ............... 607/2 |
| 6,364,824 B1 | * | 4/2002 | Fitzsimmons ............... 600/13 |
| 6,561,968 B1 | * | 5/2003 | Dissing et al. .............. 600/13 |

OTHER PUBLICATIONS

Sollazzo et al. (1997) "Responses of Human MG-63 Osteosarcoma Cell Line and Human Osteoblast-Like Cells to Pulsed Electromagnetic Fields." Bioelectromagnetics 18(8): 541-547.*

Mattei et al. (1999) "Correlation between pulsed electromagnetic fields exposure time and cell proliferation increase in human osteosarcoma cell lines and human normal osteoblast cells in vitro." Bioelectromagnetics 20(3): 177-82.*

Aaron et al. (Apr. 1989) "Stimulation of experimental endochondral ossification by low-energy pulsing electromagnetic fields." J. Bone Miner Res. 4(2): 227-33.*

Yen-Patton, G.P.A. J. Cell Physiology 134:37-46 (1988).*

* cited by examiner

*Primary Examiner*—Robert S. Landsman
(74) *Attorney, Agent, or Firm*—Baker & McKenzie LLP

(57) ABSTRACT

A method for activating a vascular endothelial growth factor (VEGF) receptor of one or more cells includes positioning an electromagnetic field generator in proximity to a VEGF receptor such that the flux of an electromagnetic field generated by the electromagnetic field generator will extend through the VEGF receptor. The method also includes generating an electromagnetic field, using the electromagnetic field generator, having a rate of fluctuation that activates the VEGF receptor.

11 Claims, 10 Drawing Sheets

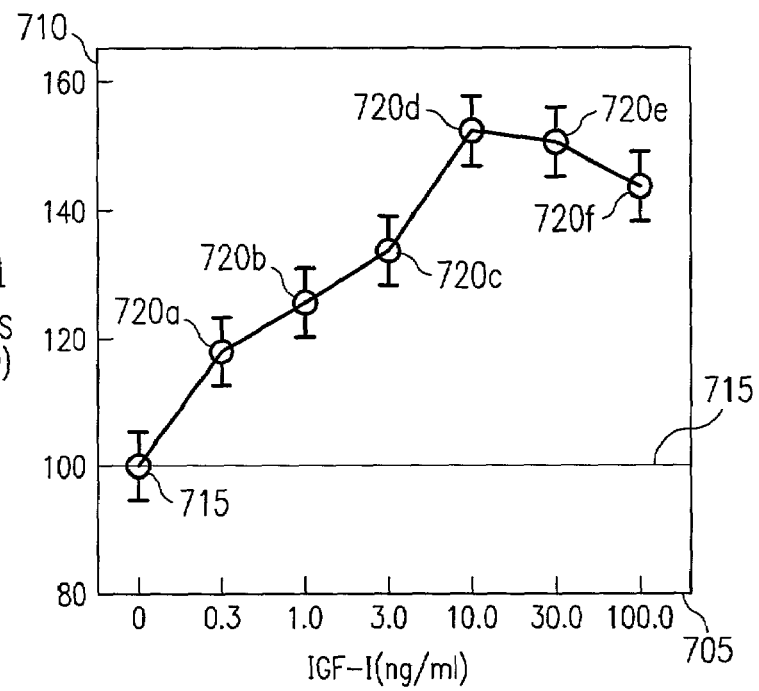
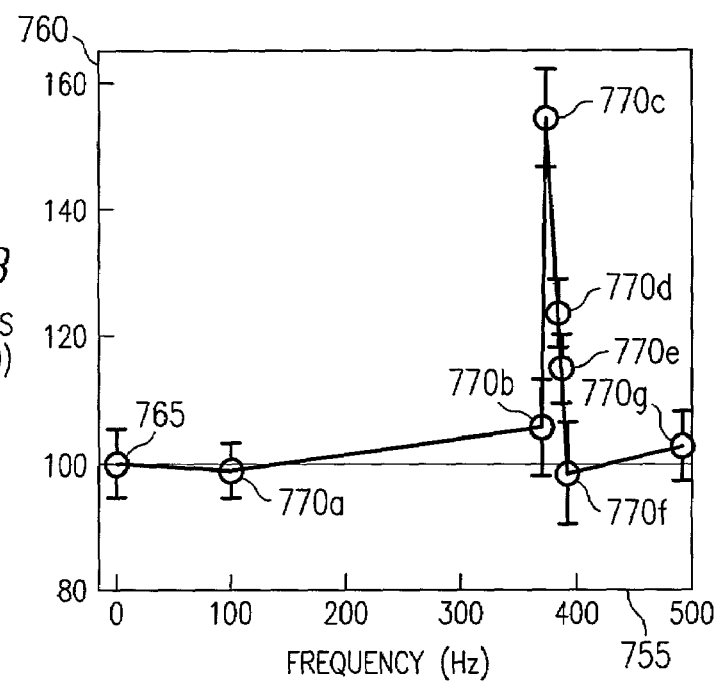

METHODS OF STIMULATING CELL RECEPTOR ACTIVITY USING ELECTROMAGNETIC FIELDS

RELATED APPLICATIONS

The instant patent application claims priority to U.S. Provisional Patent Application Ser. No. 60/271,030, filed on Feb. 23, 2001.

TECHNICAL FIELD OF THE INVENTION

This invention relates to the field of stimulating cell receptor activity, and more particularly, to using electromagnetic fields to stimulate cell receptor activity.

BACKGROUND OF THE INVENTION

Osteoporosis is a disease characterized by a decrease in bone mass which leads to a spontaneous bone fracture or fractures occurring due to an impact that under normal conditions would not produce a bone fracture. The goal for treating osteoporosis is to build bone strength to a level sufficient to withstand normal loading conditions without failure. A significant determinant of bone strength is bone mass. Bone mass is determined by the balance between the activity of osteoclast, which destroy bone, and osteoblast, which build bone. During homeostasis, in which bone mass is maintained at a constant level, the activity of the osteoclast and osteoblast are equal. Around the age of thirty, peak bone mass is typically achieved. At this stage the activity of osteoblasts begin to lag behind the activity of osteoclasts. This results in a loss of bone. The health impact of osteoporosis includes loss of the quality of life as osteoporotic bone fractures usually occur in the elderly who have a diminished healing capacity.

One method of treatment is to stimulate osteoblast to form new bone. It is well known in biology that mature, fully differentiated cells do not divide to create new cells. Therefore, to increase the number of bone producing, fully differentiated bone cells it is necessary to first increase the number of pre-osteoblast cells and then induce their maturation into fully differentiated bone cells to reverse the effects of osteoporosis. Furthermore, since new bone cell growth is also needed to heal non-osteoporotic bone fractures and to fuse vertebrae, the stimulation of osteoblasts to form new bone is also useful for treating other fractures and for performing spinal fusion.

SUMMARY OF THE INVENTION

According to the present invention, disadvantages and problems associated with previous cell growth stimulation techniques have been substantially reduced or eliminated.

According to one embodiment of the present invention, a method for activating a vascular endothelial growth factor (VEGF) receptor of one or more cells includes positioning an electromagnetic field generator in proximity to a VEGF receptor such that the flux of an electromagnetic field generated by the electromagnetic field generator will extend through the VEGF receptor. The method also includes generating an electromagnetic field, using the electromagnetic field generator, having a rate of fluctuation that activates the VEGF receptor.

In another embodiment of the present invention, a device for activating a VEGF receptor includes a generator operable to generate an electromagnetic field having a rate of fluctuation that activates the VEGF receptor. The device also includes a positioning apparatus operable to position the generator such that the flux of the electromagnetic field will extend through the VEGF receptor.

Particular embodiments of the present invention may provide one or more technical advantages. For example, certain embodiments allow for the reversal of osteoporosis and for stimulating the healing of fractures caused by osteoporosis. Certain embodiments may also be used to increase the rate of healing other bone fractures and to fuse vertebrae. These treatments may be performed without the introduction of growth factors into the body and without the expense associated with producing such growth factors.

Other technical advantages may be readily apparent to those skilled in the art from the figures, description and claims included herein.

BRIEF DESCRIPTION OF THE DRAWINGS

To provide a more complete understanding of the present invention and the features and advantages thereof, reference is made to the following description taken in conjunction with the accompanying drawings, in which:

FIG. 10A is a graph illustrating the effect of IGF-I ligands on colonies of the MG-63 osteosarcoma (MG-63) cell line;

FIG. 10B is a graph illustrating the effect of a PEMF treatment on colonies of the MG-63 cell line;

DESCRIPTION OF EXAMPLE EMBODIMENTS

Figure 1:
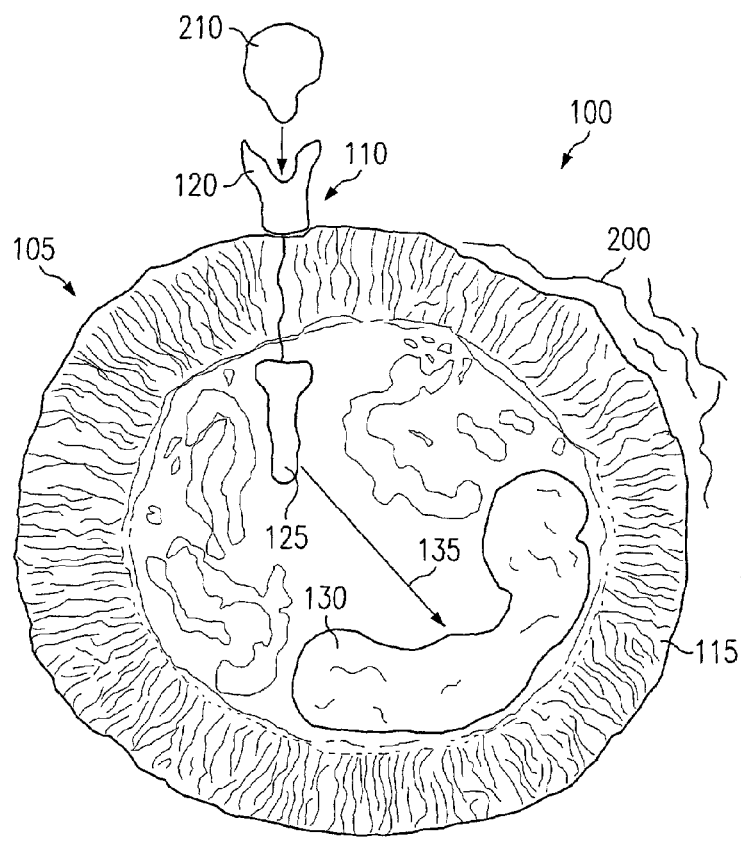
FIG. 1 illustrates an example cellular environment.

FIG. 1 illustrates an example cellular environment 100. Cellular environment 100 may include numerous cells 105 and extracellular fluid 200, although only a single cell 105 is illustrated. Cell 105 may be a bone cell, a cartilage cell, a vascular endothelial cell, or any other appropriate type of cell. Cell 105 includes one or more cell receptors 110 spanning a cell membrane 115. A cell receptor 110 is typically a protein compound composed of multiple subunits. These sub-units may include an extracellular sub-unit 120, which is outside of cell membrane 115, an intracellular sub-unit 125 which is inside cell membrane 115. Cell receptors 110 may communicate events occurring outside of cell 105 to appropriate intracellular machinery 130, such as cell nuclei.

The occurrence of certain events may be communicated to, and detected by, cell receptors 110 through the use of ligands 210. Ligands 210 are typically composed of proteins and travel through intracellular fluid 200 seeking to bind with the cell receptors 110 of cells 105. When the ligand 210 binds with a cell receptor 110, the cell receptor 110 generates a signal 135 which is delivered to the appropriate intracellular machinery 130 inside the cell 105. The signal causes the intracellular machinery 130 to perform certain specific actions. A cell receptor 110 that is bonded to ligand 210 is considered to be in an active state.

One type of ligand 210 that may interact with cell receptor 110 is a growth factor. Examples of such growth factors include, but are not limited to, an insulin-like growth factor-I (IGF-I), an epidermal growth factor (EGF), a vascular endothelial growth factor (VEGF), a basic fibroglast growth factor (bFGF), and transforming growth factor beta (TGFb). The primary function of such growth factors, as well as other ligands, is to activate specific receptors 110 located on the surface of cells 105. For example, cell receptors 110 may include an insulin-like growth factor-I (IGF-I) receptor, an epidermal growth factor (EGF) receptor, a vascular endothelial growth factor (VEGF) receptor, a basic fibroglast growth factor (bFGF) receptor, a transforming growth factor beta (TGFb) receptor, or any other appropriate receptor (some or all of these receptors 110 may be included in cell 105). As can be seen, each growth factor has an associated receptor 110 with which it binds and which it activates to initiate certain biological effects, as described below.

Figure 2:
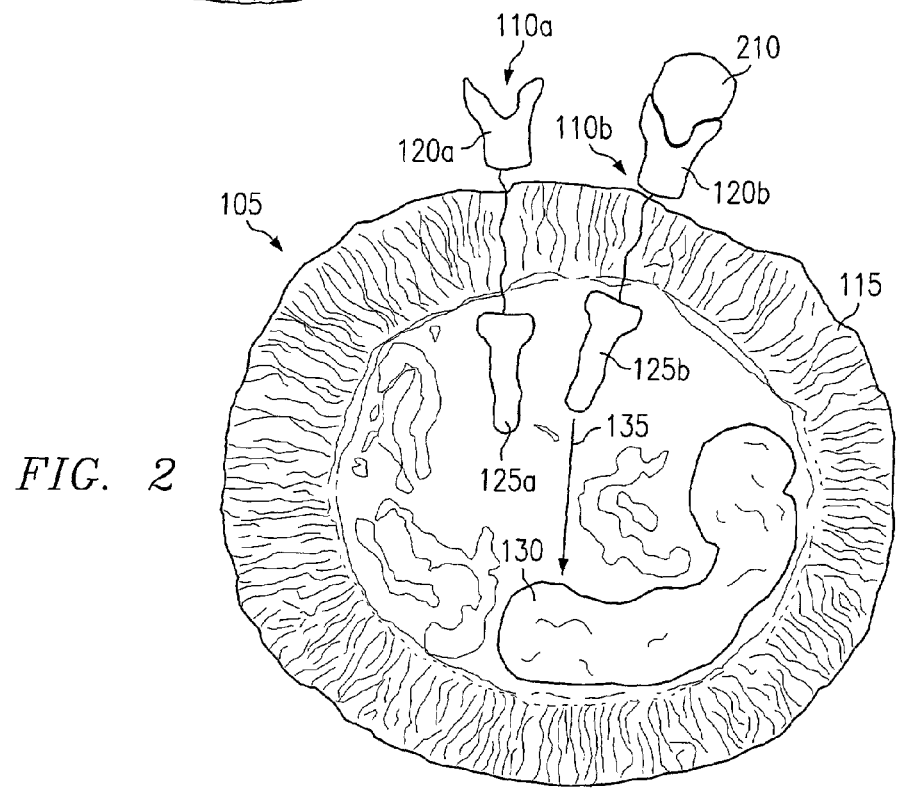
FIG. 2 illustrates an example inactive cell receptor and an example active cell receptor that has been activated by ligand.

FIG. 2 illustrates an example inactive cell receptor 110a and an example active cell receptor 110b that has been activated by ligand 210. Without the presence of a ligand 210, the intracellular sub-unit 125a and the extracellular sub-unit 120a of inactive cell receptor 110a vibrate in a specific relationship to each other. However, when a ligand 210 binds itself to a cell receptor 110 and activates the cell receptor 110, as shown with active cell receptor 110b, mass is added to extracellular sub-unit 120b. This added mass changes the manner in which the intracellular sub-unit 125b and the extracellular sub-unit 120b vibrate with respect to each other. This change in vibration is then detected or sensed by the intracellular machinery 130. For example, intracellular machinery 130 may receive a signal 135 generated by intracellular sub-unit 125b in response to the change in vibration.

The activation of such receptors and the resultant detection of this change in vibration may cause various actions to occur, depending on the type of receptor 110 that is activated. For example, when a growth factor ligand 210 activates a receptor 110 associated with that growth factor, receptor 110 may generate a signal 135 instructing the intracellular machinery 130 of a pre-osteoblast cell 105 to initiate the division of the cell 105. The activation of another type of receptor 110 by a different growth factor ligand 210 may cause a signal 135 to be generated instructing the intracellular machinery 130 of a cell 105 to differentiate the cell 105 into a particular type of cell, such as a bone cell. Since such cell division and differentiation are required for the development of new bone cells that are necessary to cure osteoporosis and to heal a bone fracture, growth factor ligands 210 and the resulting reactions that are caused when these ligands 210 activate an associated receptor 110 are integral to the natural process of bone cell growth.

Although this receptor activation occurs naturally and regularly in the human body, external sources may be used to change the manner in which an intracellular sub-unit 125 and an extracellular sub-unit 120 vibrate, so as to stimulate bone cell growth. For example, growth factor ligands 210 may be artificially introduced into or stimulated in a person's body to increase the activation of appropriate receptors 110 so as to stimulate cell division and differentiation and help cure osteoporosis and heal bone fractures (or fuse vertebrae). This same cell division and differentiation may also result if alternative techniques are used to activate particular receptors 110. One such technique involves the use of an electromagnetic field (or a magnetic field) to activate receptors 110.

Figure 3:
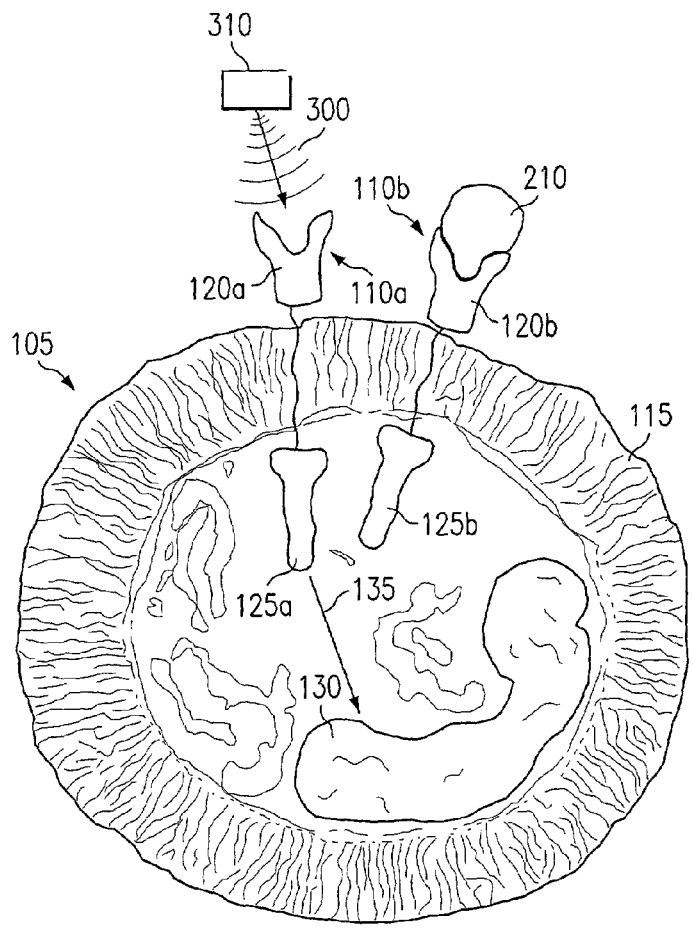
FIG. 3 illustrates an example use of an electromagnetic field to induce cell receptor activity.

FIG. 3 illustrates an example use of an electromagnetic field 300 to induce cell receptor activity. Although cell receptors 110 are naturally activated through the action of ligands 210, receptors 110 may also be activated using electromagnetic field 300. To stimulate cell receptor activity, such as cell growth or differentiation, a generator 310 generates an electromagnetic field 300 with a predetermined frequency component to interact with specific cell receptors 110 of cells 105 targeted for activity. The term "electromagnetic field" shall be construed to include both electromagnetic fields and magnetic fields. The electromagnetic field 300 causes intracellular sub-unit 125a and extracellular sub-unit 120a to vibrate in a manner simulating the vibrations an activated cell receptor 110b. These vibrations are detected by intracellular machinery 130 and result in the same biological activity that occurs in response to the activation of cell receptor 110b (assuming that receptors 110a and 110b are the same type of receptor). For example, the vibrations induced by electromagnetic field 300 may stimulate cell division or differentiation. Therefore, generator 310 may be used to help cure or prevent osteoporosis, heal bone fractures, and fuse vertebrae.

Figure 4:
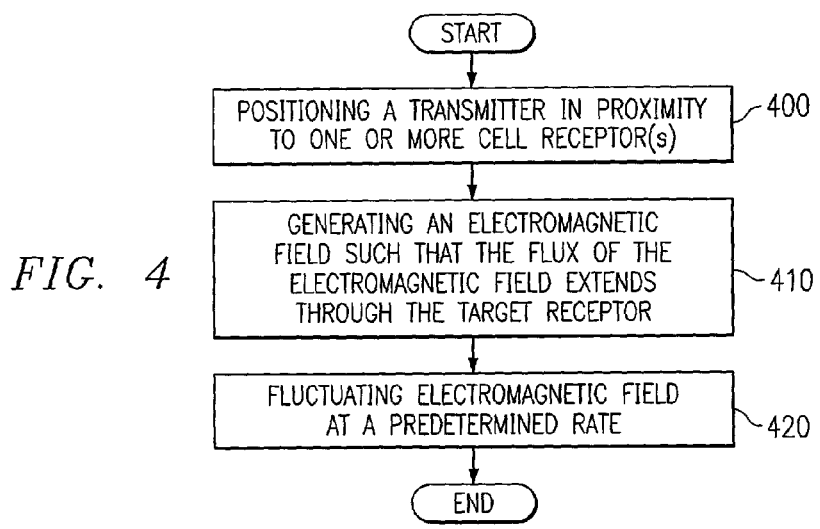
FIG. 4 illustrates an example method for activating a cell receptor.

FIG. 4 illustrates an example method for activating a cell receptor 110. The method begins at step 400 where generator 310 is positioned in proximity to one or more target cell receptors 110. Particular types of receptors 110 in particular types of cells 105 may be targeted based on specific biological actions that are desired. For example, as described below, activation of VEGF receptors 110 in bone and vascular endothelial cells using an electromagnetic field 300 will typically increase cell growth in these cells 105. Activation of other receptors 110 may produce the same or a different biological effect. At step 410, an electromagnetic field 300 is generated such that the flux of the electromagnetic field 300 extends through the target cell receptors 110. The electromagnetic field 300 is fluctuated or pulsed at a predetermined rate at step 420 for a desired amount of time. This type of fluctuating electromagnetic field 300 may be referred to as a pulsed electromagnetic field (PEMF) and, similarly, generator 310 may be referred to as a PEMF generator or stimulator.

Figure 5:
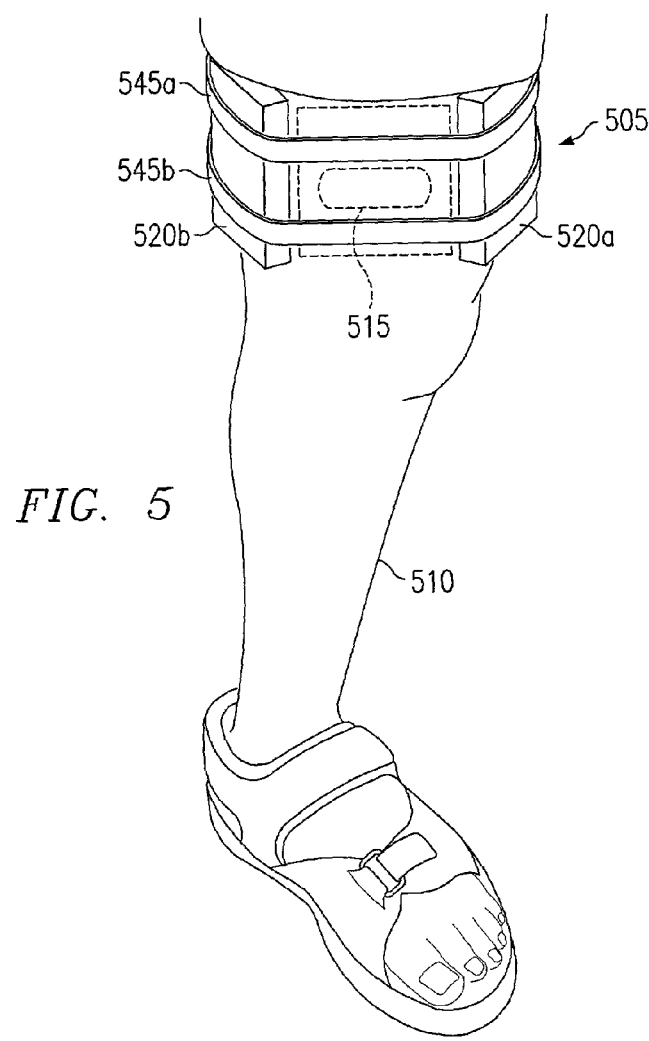
FIG. 5 illustrates an example cell receptor activating device positioned on a limb of a patient.

FIG. 5 illustrates an example cell receptor activating device 505 positioned on a limb 510 of a patient. The area to be treated ("treatment area") 515 may be on the surface of limb 510 or within the limb 510. Alternatively or additionally, the treatment area may be any other part of body or any other area that contains cells having receptors that may be activated. The example cell receptor activating device 505 includes two PEMF generators 520a and 520b capable of generating an electromagnetic field. PEMF generators 520a and 520b are positioned in proximity to treatment area 515 such that the flux of the electromagnetic field extends through the target cell receptors. PEMF generators 520a and 520b may be positioned using bands 545 (which may include straps, belts, ties, or the like); using clamps or adhesive; by integrating generators 520a and 520b in a cast, an orthopedic device, an orthopedic support; or using any other appropriate attachment or positioning techniques.

Figure 6:
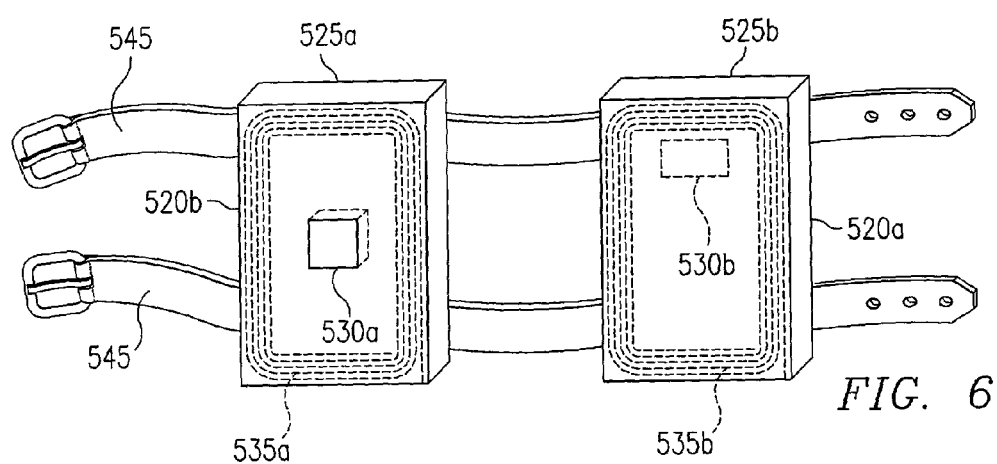
FIG. 6 illustrates example pulsed electromagnetic field (PEMF) generators of an example cell receptor activating device.

FIG. 6 illustrates example PEMF generators 520a and 520b in further detail. Each PEMF generator 520a, 520b includes a housing 525a, 525b of a non-magnetic material, such as plastic, which encloses a field coil 535a, 535b. Each PEMF generator 520a, 520b also includes an alternating current (AC) source 530a, 530b that is electrically coupled to each field coil 535a, 535b. The AC current source 530a, 530b is capable of generating an AC current with a predetermined rate of fluctuation, which flows through the field coils 535a, 535b. The predetermined rate of fluctuation can be set by the user, can be preset in accordance with manufacturing specifications, or can be selected in any other appropriate way. When the AC current flows through field coils 535a, 535b, an electromagnetic field is generated. Additionally, the magnitude of the electromagnetic field is proportional to the instantaneous magnitude of the AC current. Therefore, the electromagnetic field fluctuates or pulses at the predetermined rate of fluctuation of the AC current, thus generating a PEMF.

Figure 7A:
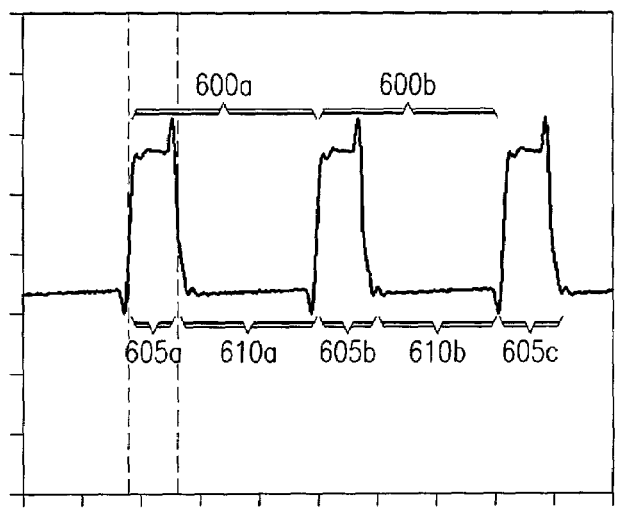
FIGS. 7A through 7C illustrate an example output waveform of an electromagnetic field that may be generated by PEMF generators.

FIG. 7A illustrates an example output waveform of an electromagnetic field that may be generated by PEMF generators 520a and 520b. The example waveform includes a series of bursts that each include multiple pulses 600. In the portion of the waveform illustrated in FIG. 7A, parts of three different pulses 600 are illustrated. Each pulse 600 includes a first pulse portion 605 that is followed by a second pulse portion 610. Each pulse portion 605 has a duration of approximately four microseconds (4 μsec) and each pulse portion 610 has a duration of approximately twelve microseconds (12 μsec). Therefore, the pulse period of each pulse 600 is approximately sixteen microseconds (16 μsec). The pulse frequency is thus approximately 62,500 Hertz (Hz). It should be notes that in all potential waveforms generated by PEMF generators 520a and 520b, the pulse frequency may be the rate of fluctuation of the magnetic field, as described above, or the rate of fluctuation may refer to any other appropriate frequencies associated with a waveform, such as the burst frequency.

Figure 7B:
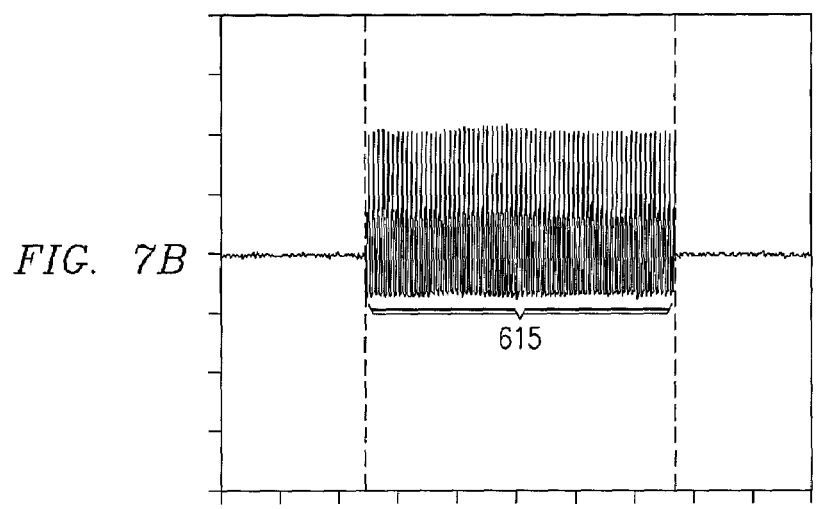
Figure 7C:
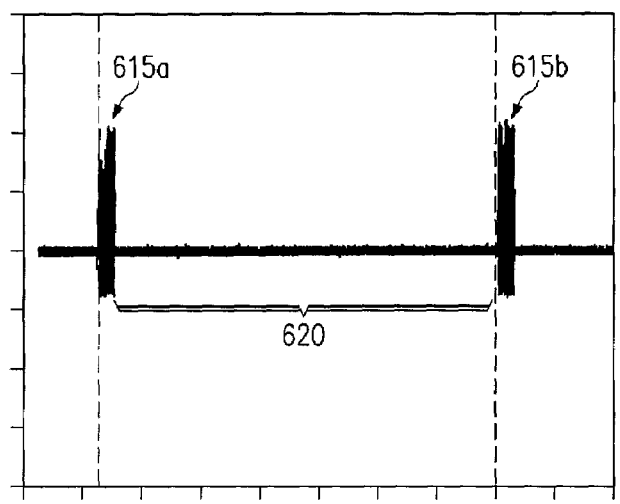

FIG. 7B illustrates a greater portion of the example waveform of FIG. 7A. As is illustrated, the waveform includes a burst 615 that includes numerous pulses 600. For example, the illustrated waveform delivers a burst 615 that includes 1609 pulses during a burst period. The example burst 615 has a burst period of approximately twenty-six milliseconds (26 msec). As is illustrated in FIG. 7C, each burst 615 is followed by an inter-burst period 620. The example waveform includes a burst 615 approximately every 668 milliseconds (msec).

Figure 8A:
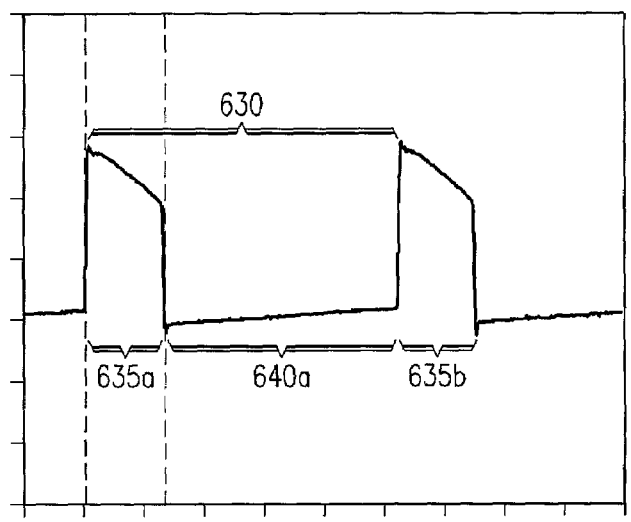
FIGS. 8A through 8C illustrate another example output waveform of an electromagnetic field that may be generated by PEMF generators.

FIG. 8A illustrates another example output waveform of an electromagnetic field that may be generated by PEMF generators 520a and 520b. The example waveform includes a series of bursts that each include multiple pulses 630. In the portion of the waveform illustrated in FIG. 8A, parts of two different pulses 630 are illustrated. Each pulse 630 includes a first pulse portion 635 that is followed by a second pulse portion 640. Each pulse portion 635 has a duration of approximately sixty-five microseconds (65 μsec) and each pulse portion 640 has a duration of approximately one hundred ninety-six microseconds (196 μsec). Therefore, the pulse period of each pulse 630 is approximately two hundred sixty-one microseconds (261 μsec). The pulse frequency is thus approximately 3831 Hertz (Hz).

Figure 8B:
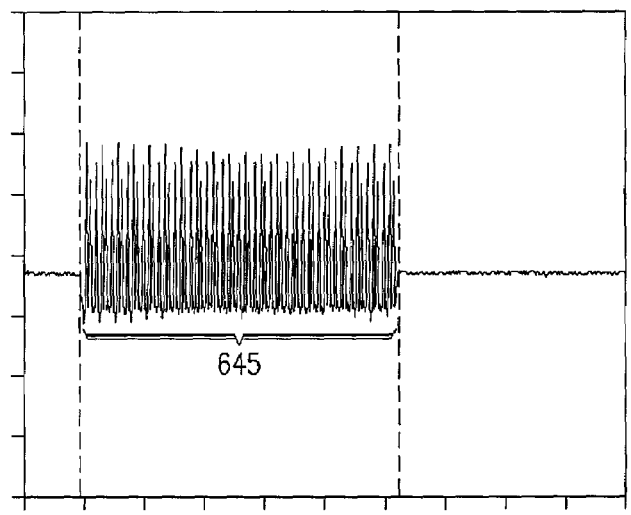
Figure 8C:
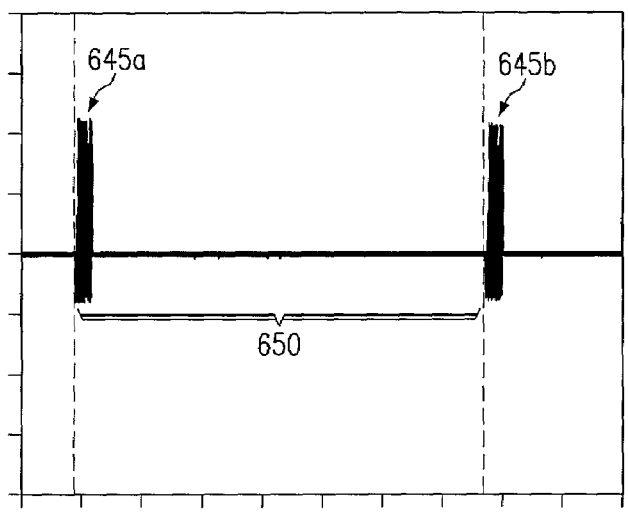

FIG. 8B illustrates a greater portion of the example waveform of FIG. 8A. As is illustrated, the waveform includes a burst 645 that includes numerous pulses 630. For example, the illustrated waveform delivers a burst 645 that includes ninety-nine pulses during a burst period. The example burst 645 has a burst period of approximately twenty-six milliseconds (26 msec). As is illustrated in FIG. 8C, each burst 645 is followed by an inter-burst period 650. The example waveform includes a burst 645 approximately every 668 milliseconds (msec).

Figure 9A:
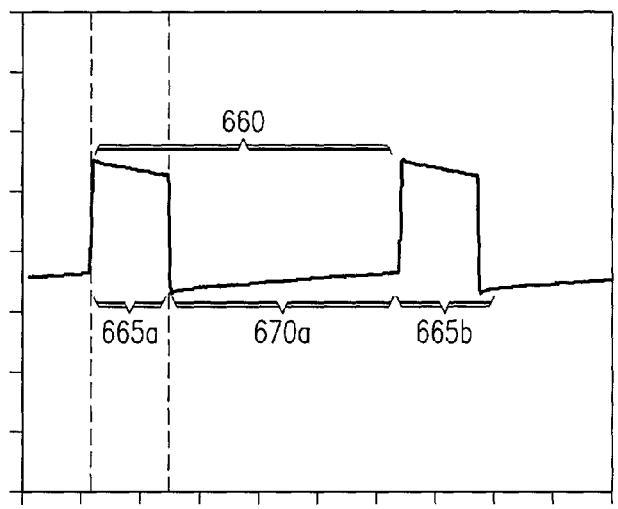
FIGS. 9A through 9C illustrate yet another example output waveform of an electromagnetic field that may be generated by PEMF generators.

FIG. 9A illustrates yet another example output waveform of an electromagnetic field that may be generated by PEMF generators 520a and 520b. The example waveform includes a series of bursts that each include multiple pulses 660. In the portion of the waveform illustrated in FIG. 9A, parts of two different pulses 660 are illustrated. Each pulse 660 includes a first pulse portion 665 that is followed by a second pulse portion 670. Each pulse portion 665 has a duration of approximately sixty-five microseconds (65 μsec) and each pulse portion 670 has a duration of approximately one hundred ninety-four microseconds (194 μsec). Therefore, the pulse period of each pulse 660 is approximately two hundred fifty-nine microseconds (259 μsec). The pulse frequency is thus approximately 3861 Hertz (Hz).

Figure 9B:
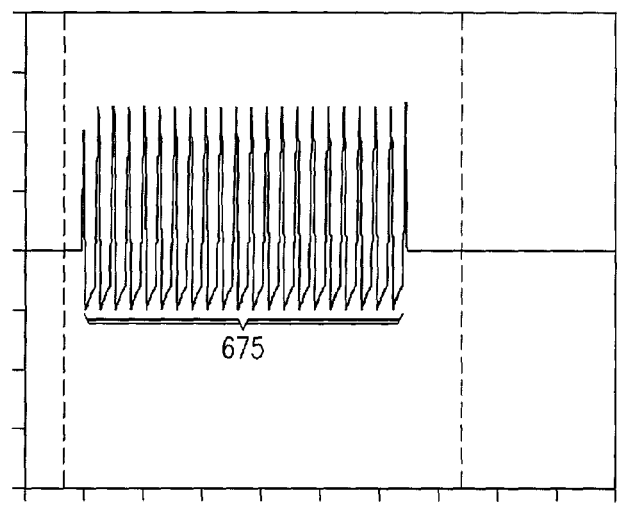
Figure 9C:
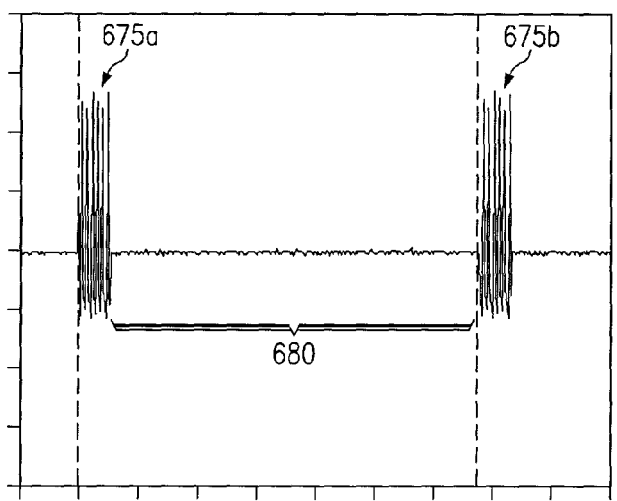

FIG. 9B illustrates a greater portion of the example waveform of FIG. 9A. As is illustrated, the waveform includes a burst 675 that includes numerous pulses 660. For example, the illustrated waveform delivers a burst 675 that includes twenty-one pulses during a burst period. The example burst 675 has a burst period of approximately 5.5 milliseconds (msec). As is illustrated in FIG. 9C, each burst 675 is followed by an inter-burst period 680. The example waveform includes a burst 675 approximately every 67.4 milliseconds (msec).

Although example output waveforms have been illustrated in FIGS. 7A through 9C, it should be understood that any other appropriate waveforms may be generated. Furthermore, particular waveforms may be used to treat particular conditions. As an example only and not by way of limitation, the waveform illustrated in FIGS. 7A through 7C may be used to treat osteoporosis, the waveform illustrated in FIGS. 8A through 8C may be used for spinal fusion, and the waveform illustrated in FIGS. 9A through 9C may be used to treat a bone fracture. It should be noted that these waveforms may be used to successfully treat other conditions and that other waveforms may be used to treat the listed conditions. Moreover, it should be understood that the illustrated waveforms and their specified parameters may be modified and still produce the same effect.

FIG. 10A is a graph illustrating the effect of IGF-I ligands on colonies of the MG-63 osteosarcoma (MG-63) cell line. The graph illustrates the results of an experiment in which colonies of the MG-63 cell line were treated with IGF-I ligands. Cells of the MG-63 cell line are known for their ability to grow indefinitely and for their sensitivity to the IGF-I ligand. The horizontal axis 705 identifies the concentrations of various solutions of IGF-I ligands that were used to treat different MG-63 cell line colonies of equal cell count. The vertical axis 710 identifies the MG-63 cell count of each colony as a percentage of the cell count of a control group, represented by a control data point 715 at zero on horizontal axis 705 and at 100% on vertical axis 710. Data points 720 each represent the cell count of an MG-63 cell line colony twenty-four hours after the treatment with IGF-I ligands as a percentage of the cell count of the control group. As can be seen from the graph, data points 720 establish that the MG-63 cells proliferate when treated with the IGF-I ligand (since all data points 720 have a larger vertical axis value than control data point 715). Data point 720d, at which peak cell count was achieved, represents a treatment with a ten nanogram/milliliter IGF-I ligand solution.

FIG. 10B is a graph illustrating the effect of PEMF treatment on colonies of the MG-63 cell line. The horizontal axis 755 identifies the various rates of fluctuation of an electromagnetic field applied to different MG-63 cell line colonies of equal cell count. The vertical axis 760 identifies the cell count of each treated MG-63 cell line colony as a percentage of the cell count of a control group. The control group is represented by a control data point 765 at zero on horizontal axis 755 and at 100% on vertical axis 760. Data points 770 each represent the cell count of an MG-63 cell line colony twenty-four hours after the treatment with electromagnetic fields as a percentage of the cell count of the control group. The cell count results suggest no statistically significant effect for any rate of fluctuation below approximately 375 Hz and any rate of fluctuation above approximately 385 Hz. However, the cell count of the MG-63 cell line colonies which were exposed to electromagnetic fields which fluctuated at rates between approximately 375 Hz and 385 Hz, represented by data points 770c, 770d, and 770e, rose sharply (with the peak cell count achieved at a fluctuation rate of approximately 379 Hz).

The peak cell count of 150%, represented by plot 770c, mimics the peak cell count, data point 720d, achieved with the IGF-I ligand solution treatment. Accordingly, IGF-I receptors can be activated, thereby stimulating the growth of MG-63 cells 105, using an electromagnetic field generated by a PEMF generator in a manner similar to the activation of IGF-I receptors using IGF-I ligands.

Figure 11A:
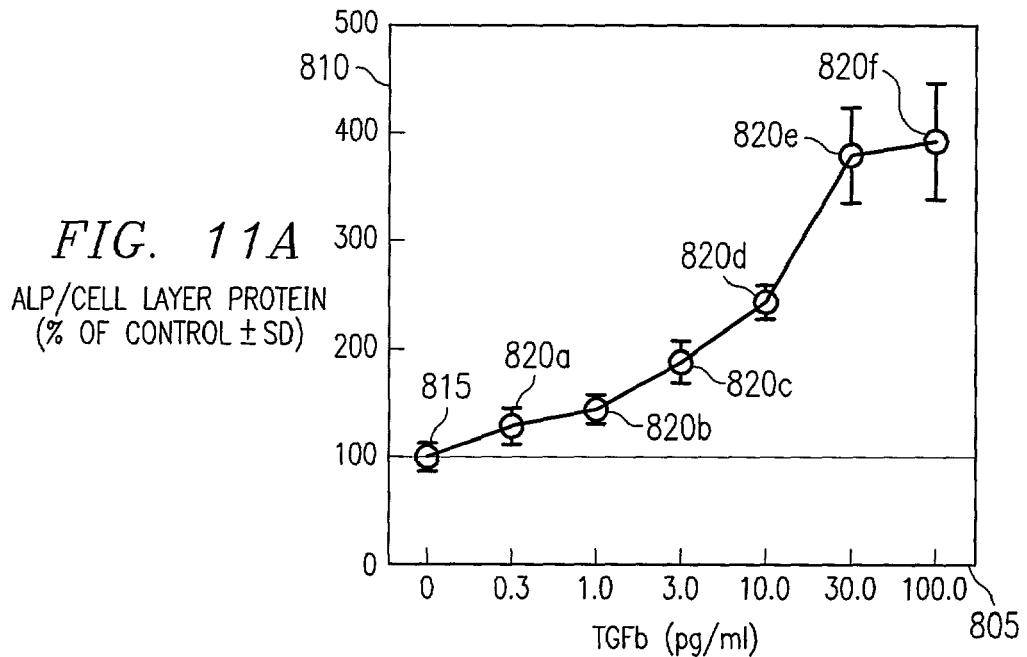
FIG. 11A is a graph illustrating the effect of TGFb ligands on colonies of the MG-63 cell line.

FIG. 11A is a graph illustrating the effect of TGFb ligands on colonies of the MG-63 cell line. The horizontal axis 805 identifies the concentrations of various solutions of TGFb ligands which were used to treat different MG-63 cell line colonies of equal alkaline phosphatase (ALP) activity. ALP activity is commonly used to measure bone cell differentiation. The vertical axis 810 identifies the ALP activity of each MG-63 cell line colony as a percentage of the ALP activity of a control group, which is represented by a data point 815 at zero on horizontal axis 805 and at 100% on vertical axis 810. The ALP activity of each MG-63 cell line as a percentage of the cell count of the control group colony seventy-two hours after the treatment is represented by data points 820. Data points 820 establish that ALP activity is increased, and therefore bone cell differentiation is increased, in the MG-63 cells when treated with the TGFb ligand solution. Data points 820e and 820f, associated with a plateau at which peak ALP activity is achieved, represents a treatment with TGFb solutions having a concentration greater than thirty picograms/milliliter.

Figure 11B:
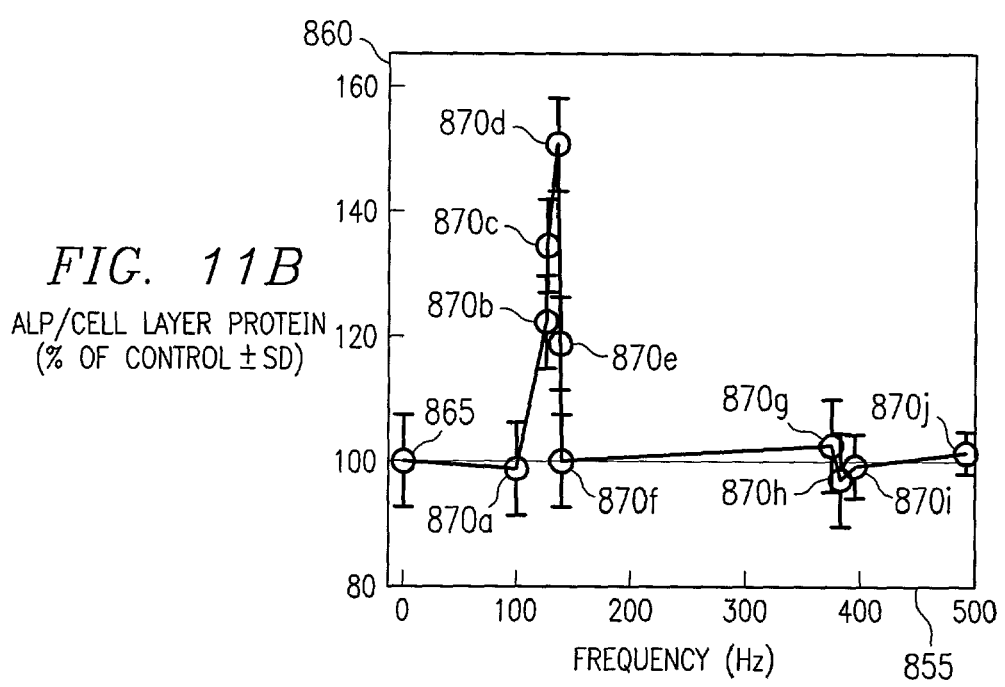
FIG. 11B is a graph illustrating the effect of another PEMF treatment on colonies of the MG-63 cell line.

FIG. 11B is a graph illustrating the effect of another PEMF treatment on colonies of the MG-63 cell line. The horizontal axis 855 measures the rate of fluctuation of an electromagnetic field applied to various MG-63 cell line colonies of equal ALP activity. The vertical axis 860 measures the ALP activity of each MG-63 cell line colony as a percentage of the ALP activity of a control group, which is represented by a data point 865 at zero on horizontal axis 855 and at 100% on vertical axis 860. The ALP activity of each MG-63 cell line seventy-two hours after PEMF treatment as a percentage of the ALP activity of the control group is represented by data points 870. Data points 870 suggest no statistically significant effect for rates of fluctuation below approximately 130 Hz and rates of fluctuation above approximately 140 Hz. However, the ALP activity, and therefore cell differentiation, of the MG-63 cell line colonies which were exposed to electromagnetic fields which fluctuated at rates between approximately 130 Hz and 140 Hz (represented by data points 870b, 870c, 870d, and 870e) rose sharply. The highest ALP activity/cell differentiation rate was achieved with a fluctuation rate of approximately 133 Hz.

Accordingly, TGFb receptors can be activated, thereby stimulating the differentiation of MG-63 cells by exposing the receptors to an electromagnetic field fluctuating at a rate between approximately 130 Hz and 140 Hz. Additionally, no statistically significant activity occurred when the electromagnetic field was fluctuated at rates between 375 Hz to 385 Hz (the optimal rates for activating an IGF-I receptor illustrated in FIG. 10B). The foregoing leads to the conclusion that fluctuating the electromagnetic field at a predetermined rate activates only certain receptors. Furthermore, an electromagnetic field having a particular rate of fluctuation may also be used to stimulate cell growth by activating other types of growth factor receptors, such as VEGF receptors, in a similar manner. Therefore, an electromagnetic field having a particular fluctuation rate can be generated in proximity to one or more cells having multiple types of receptors, but only particular cell receptors may be activated according to the chosen fluctuation rate. Since activation of different types of cell receptors may cause different types of biological activity, the fluctuation may be selected so as to create a desired biological effect (such as cell growth or differentiation).

Additional experimentation has shown that various growth factors, such as IGF-I, EGF, VEGF, and bFGF, also cause biological effects (such as cell growth) in normal human bone cells (HBC), normal human cartilage cells (HCC), and normal human vascular endothelial cells (Huvec). Experimentation also has shown that these normal human cell types also respond to PEMF treatment. To further advance the understanding of the biological action caused by PEMF treatment, it is useful to eliminate the effect of particular types of receptors during experimentation so as to determine the involvement of these types of receptors in PEMF treatment. One technique that may be used to eliminate the effect of a particular type of receptor is to use antibodies against particular growth factor receptors.

Figure 12:
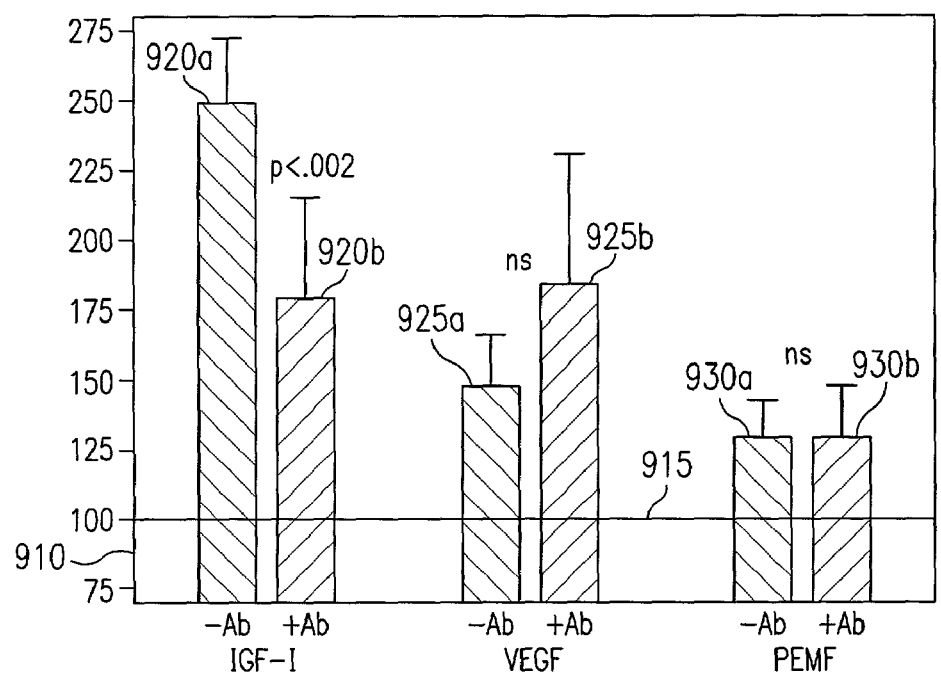
FIG. 12 is a bar graph illustrating the effect of an antibody against IGF-I receptors on treatments of bone cells with an IGF-I growth factor, a VEGF growth factor, and PEMF.

FIG. 12 is a bar graph illustrating the effect of an antibody against IGF-I receptors on treatments of bone cells with an IGF-I growth factor, a VEGF growth factor, and PEMF. As described below, this data represented in this graph shows that IGF-I receptors in normal human bone cells are not a major component in the biological mechanism of action for PEMF treatment. The vertical axis 910 of the graph identifies the bone cell count of treated bone cell colonies as a percentage of the cell count of a control group, represented by a control data line 915 at 100% on vertical axis 910. Bars 920, 925, and 930 each represent the cell count of a bone cell colony twenty-four hours after a particular treatment as a percentage of the cell count of the control group (the percent change in cell count).

More specifically, bar 920a represents the percent change in bone cell count twenty-four hours after treatment with an IGF-I growth factor. Bar 920b represents the percent change in cell count twenty-four hours after treatment with an IGF-I growth factor, but where an antibody against the IGF-I receptor (αIR3) was added to the colony before the treatment. As is shown by the lower percent change represented by bar 920b as compared to bar 920a, the addition of the IGF-I antibody decreased cell growth resulting from the introduction of IGF-I growth factor, as compared to the results where no IGF-I receptor antibody was introduced. This is to be expected since the IGF-I receptor antibody impedes the activation of the IGF-I receptor.

Bar 925a represents the percent change in bone cell count twenty-four hours after treatment with a VEGF growth factor. Bar 925b represents the percent change in cell count twenty-four hours after treatment with an VEGF growth factor, but where the antibody to the IGF-I receptor (αIR3) was added to the colony before the treatment. As is shown by the higher percent change represented by bar 925b as compared to bar 925a, the addition of the IGF-I antibody increased bone cell growth resulting from the introduction of VEGF growth factor, as compared to the results where no IGF-I receptor antibody was introduced.

Bar 930a represents the percent change in cell count twenty-four hours after a PEMF treatment. The PEMF treatment used included electromagnetic fields having a waveform the same as or similar to the waveform described in relation to FIGS. 8A through 8C. Bar 930b represents the percent change in cell count twenty-four hours after PEMF treatment, but where the antibody to the IGF-I receptor (αIR3) was added to the colony before the treatment. As is shown, the IGF-I receptor antibody has no effect on the percent change in cell growth resulting from PEMF treatment.

In summary, the data in the graph shows that normal human bone cells respond to growth factors such as IGF-I and VEGF with an increase in cell growth (as indicated by bars 920a and 925a). Furthermore, treatment with PEMF also increases cell growth (as indicated by bar 930a). When an antibody that blocks the IGF-I receptor is added prior to experimental treatment, the effect of PEMF exposure is not blocked. Furthermore, the fact that the antibody is blocking IGF-I action, but not VEGF action, indicates that the antibody is acting specifically against the IGF-I receptor. Since the antibody did not block the action of the PEMF treatment, this suggests that the PEMF is not acting through the IGF-I receptor.

Figure 13:
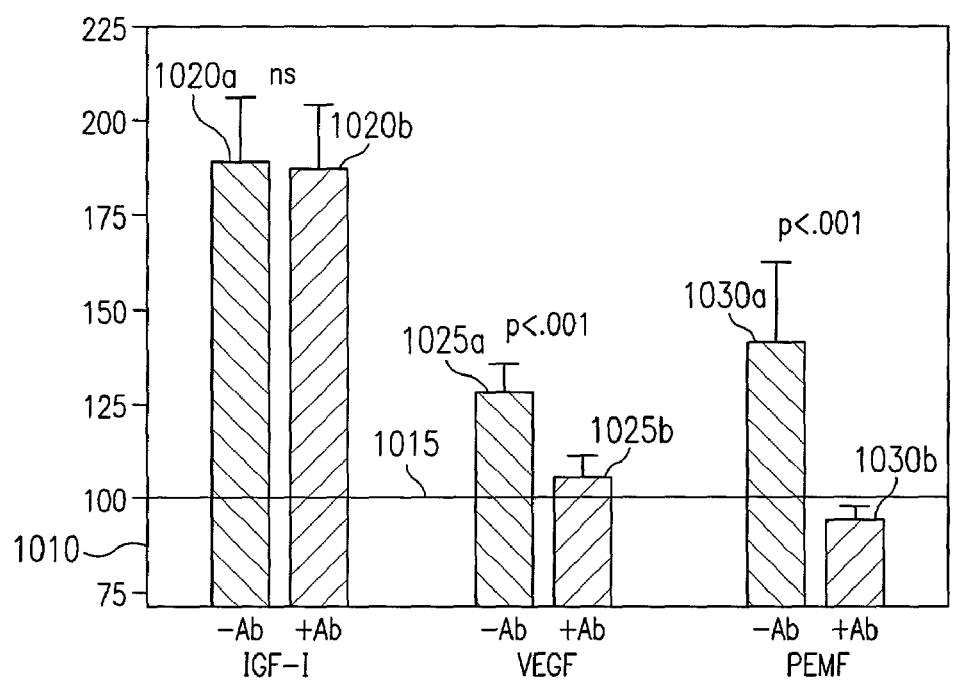
FIG. 13 is a bar graph illustrating the effect of an antibody against VEGF receptors on treatments of bone cells with an IGF-I growth factor, a VEGF growth factor, and PEMF.

FIG. 13 is a bar graph illustrating the effect of an antibody against VEGF receptors on treatments of bone cells with an IGF-I growth factor, a VEGF growth factor, and PEMF. As described below, this data represented in this graph shows that VEGF receptors in normal human bone cells are a factor in the biological mechanism of action for PEMF treatment. The vertical axis 1010 of the graph identifies the bone cell count of treated bone cell colonies as a percentage of the cell count of a control group, represented by a control data line 1015 at 100% on vertical axis 1010. Bars 1020, 1025, and 1035 each represent the cell count of an bone cell colony twenty-four hours after a particular treatment as a percentage of the cell count of the control group (the percent change in cell count).

More specifically, bar 1020a represents the percent change in cell count twenty-four hours after treatment with an IGF-I growth factor. Bar 1020b represents the percent change in cell count twenty-four hours after treatment with an IGF-I growth factor, but where an antibody against the VEGF receptor was added to the colony before the treatment. As is shown, the VEGF receptor antibody has no substantial effect on the percent change in bone cell growth resulting from treatment with an IGF-I growth factor.

Bar 1025a represents the percent change in bone cell count twenty-four hours after treatment with a VEGF growth factor. Bar 1025b represents the percent change in cell count twenty-four hours after treatment with an VEGF growth factor, but where the antibody to the VEGF receptor was added to the colony before the treatment. As is shown by the lower percent change represented by bar 1025b as compared to bar 1025a, the addition of the VEGF antibody decreased bone cell growth resulting from the introduction of VEGF growth factor, as compared to the results where no VEGF receptor antibody was introduced. This is to be expected since the VEGF receptor antibody impedes the activation of the VEGF receptor.

Bar 1030a represents the percent change in bone cell count twenty-four hours after a PEMF treatment. The PEMF treatment used included electromagnetic fields having a waveform the same as or similar to the waveform described in relation to FIGS. 8A through 8C. Bar 1030b represents the percent change in cell count twenty-four hours after PEMF treatment, but where the antibody to the VEGF receptor was added to the colony before the treatment. As is shown by the lower percent change represented by bar 1030b as compared to bar 1030a, the addition of the VEGF antibody decreased bone cell growth resulting from PEMF treatment, as compared to the results where no VEGF receptor antibody was introduced.

In summary, the data in the graph shows (as with the graph of FIG. 12) that normal human bone cells respond to growth factors such as IGF-I and VEGF with an increase in cell growth (as indicated by bars 1020a and 1025a). Furthermore, treatment with PEMF also increases bone cell growth (as indicated by bar 1030a). However, when an antibody that blocks the VEGF receptor is added prior to experimental treatment, the effect of PEMF exposure is blocked. The antibody appears to be acting specifically since it blocked the action of the VEGF growth factor, but did not block the action of the IGF-I growth factor. Since the VEGF antibody also blocked the action of PEMF, this suggests that PEMF is acting through the VEGF receptor, or at least requires an active VEGF receptor to be effective.

Figure 14:
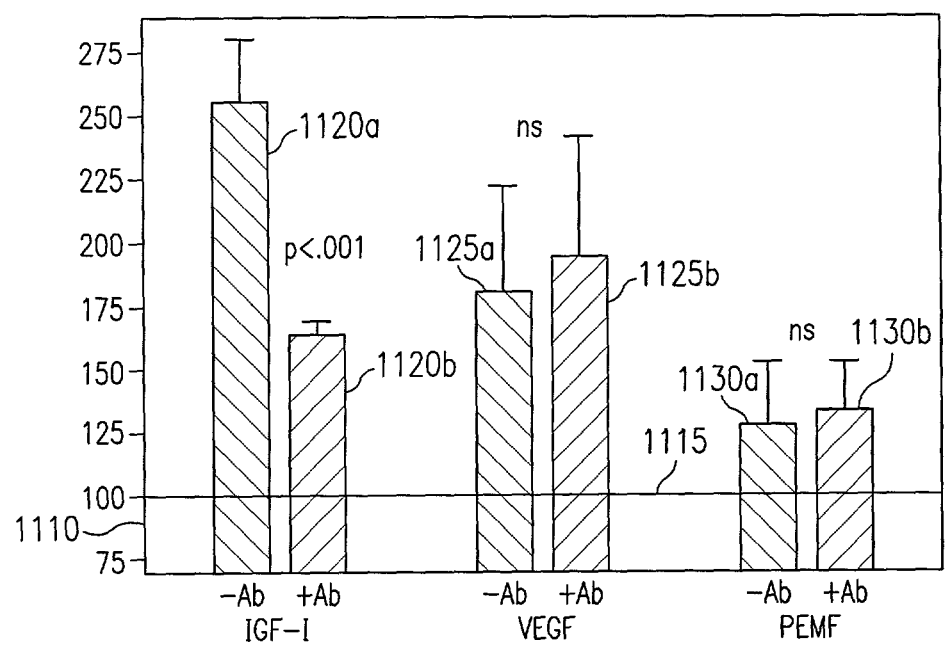
FIG. 14 is a bar graph illustrating the effect of an antibody against IGF-I receptors on treatments of vascular endothelial cells with an IGF-I growth factor, a VEGF growth factor, and PEMF.

FIG. 14 is a bar graph illustrating the effect of an antibody against IGF-I receptors on treatments of vascular endothelial cells with an IGF-I growth factor, a VEGF growth factor, and PEMF. As described below, this data represented in this graph shows that IGF-I receptors in normal human vascular endothelial cells, as in normal human bone cells, are not a major component in the biological mechanism of action for PEMF treatment. The vertical axis 1110 of the graph identifies the vascular endothelial cell count of treated vascular endothelial cell colonies as a percentage of the cell count of a control group, represented by a control data line 1115 at 100% on vertical axis 1110. Bars 1120, 1125, and 1130 each represent the cell count of an vascular endothelial cell colony twenty-four hours after a particular treatment as a percentage of the cell count of the control group (the percent change in cell count).

More specifically, bar 1120a represents the percent change in cell count twenty-four hours after treatment with an IGF-I growth factor. Bar 1120b represents the percent change in cell count twenty-four hours after treatment with an IGF-I growth factor, but where an antibody against the IGF-I receptor was added to the colony before the treatment. As is shown by the lower percent change represented by bar 1120b as compared to bar 1120a, the addition of the IGF-I antibody decreased cell growth resulting from the introduction of IGF-I growth factor, as compared to the results where no IGF-I receptor antibody was introduced. This is to be expected since the IGF-I receptor antibody impedes the activation of the IGF-I receptor.

Bar 1125a represents the percent change in cell count twenty-four hours after treatment with a VEGF growth factor. Bar 1125b represents the percent change in cell count twenty-four hours after treatment with an VEGF growth factor, but where the antibody to the IGF-I receptor was added to the colony before the treatment. As is shown by the higher percent change represented by bar 1125b as compared to bar 1125a, the addition of the IGF-I antibody increased cell growth resulting from the introduction of VEGF growth factor, as compared to the results where no IGF-I receptor antibody was introduced.

Bar 1130a represents the percent change in cell count twenty-four hours after a PEMF treatment. The PEMF treatment used included electromagnetic fields having a waveform the same as or similar to the waveform described in relation to FIGS. 8A through 8C. Bar 1130b represents the percent change in cell count twenty-four hours after PEMF treatment, but where the antibody to the IGF-I receptor was added to the colony before the treatment. As is shown, the IGF-I receptor antibody has no effect on the percent change in cell growth resulting from PEMF treatment.

In summary, the data in the graph of FIG. 14 shows that normal human vascular endothelial cells respond to growth factors such as IGF-I and VEGF with an increase in cell growth (as indicated by bars 1120a and 1125a). Furthermore, treatment with PEMF also increases cell growth (as indicated by bar 1130a). When an antibody that blocks the IGF-I receptor is added prior to experimental treatment, the effect of PEMF exposure is not blocked. Furthermore, the fact that the antibody is blocking IGF-I action, but not VEGF action, indicates that the antibody is acting specifically against the IGF-I receptor. Since the antibody did not block the action of the PEMF treatment, this suggests (as the data in FIG. 12) that the PEMF is not acting through the IGF-I receptor.

Figure 15:
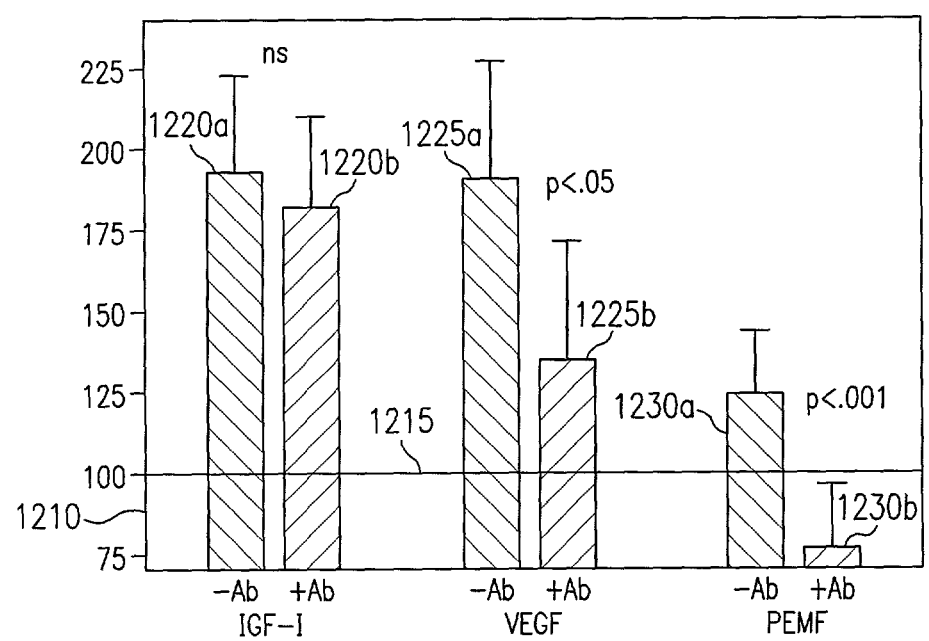
FIG. 15 is a bar graph illustrating the effect of an antibody against VEGF receptors on treatments of vascular endothelial cells with an IGF-I growth factor, a VEGF growth factor, and PEMF.

FIG. 15 is a bar graph illustrating the effect of an antibody against VEGF receptors on treatments of vascular endothelial cells with an IGF-I growth factor, a VEGF growth factor, and PEMF. As described below, this data represented in this graph shows that VEGF receptors in normal human vascular endothelial cells are a factor in the biological mechanism of action for PEMF treatment. The vertical axis 1210 of the graph identifies the vascular endothelial cell count of treated vascular endothelial cell colonies as a percentage of the cell count of a control group, represented by a control data line 1215 at 100% on vertical axis 1210. Bars 1220, 1225, and 1235 each represent the cell count of an vascular endothelial cell colony twenty-four hours after a particular treatment as a percentage of the cell count of the control group (the percent change in cell count).

More specifically, bar 1220a represents the percent change in cell count twenty-four hours after treatment with an IGF-I growth factor. Bar 1220b represents the percent change in cell count twenty-four hours after treatment with an IGF-I growth factor, but where an antibody against the VEGF receptor was added to the colony before the treatment. As is shown, the VEGF receptor antibody has a small effect on the percent change in vascular endothelial cell growth resulting from treatment with an IGF-I growth factor.

Bar 1225a represents the percent change in vascular endothelial cell count twenty-four hours after treatment with a VEGF growth factor. Bar 1225b represents the percent change in cell count twenty-four hours after treatment with an VEGF growth factor, but where the antibody to the VEGF receptor was added to the colony before the treatment. As is shown by the lower percent change represented by bar 1225b as compared to bar 1225a, the addition of the VEGF antibody decreased vascular endothelial cell growth resulting from the introduction of VEGF growth factor, as compared to the results where no VEGF receptor antibody was introduced. This is to be expected since the VEGF receptor antibody impedes the activation of the VEGF receptor.

Bar 1230a represents the percent change in vascular endothelial cell count twenty-four hours after a PEMF treatment. The PEMF treatment used included electromagnetic fields having a waveform the same as or similar to the waveform described in relation to FIGS. 8A through 8C. Bar 1230b represents the percent change in cell count twenty-four hours after PEMF treatment, but where the antibody to the VEGF receptor was added to the colony before the treatment. As is shown by the lower percent change represented by bar 1230b as compared to bar 1230a, the addition of the VEGF antibody decreased vascular endothelial cell growth resulting from PEMF treatment, as compared to the results where no VEGF receptor antibody was introduced.

In summary, the data in the graph shows (as with the graph of FIG. 14) that normal human vascular endothelial cells respond to growth factors such as IGF-I and VEGF with an increase in cell growth (as indicated by bars 1220a and 1225a). Furthermore, treatment with PEMF also increases vascular endothelial cell growth (as indicated by bar 1230a). However, when an antibody that blocks the VEGF receptor is added prior to experimental treatment, the effect of PEMF exposure is blocked. The antibody appears to be acting specifically since it blocked the action of the VEGF growth factor, but did not block the action of the IGF-I growth factor. Since the VEGF antibody also blocked the action of PEMF, this suggests (as described above with reference to bone cells) that PEMF is acting through the VEGF receptor, or at least is dependent on an active VEGF receptor to be effective.

Although the present invention has been described with several embodiments, numerous changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed is:

1. A method for activating a vascular endothelial growth factor (VEGF) receptor of one or more cells, the method comprising:

positioning an electromagnetic field generator in proximity to a VEGF receptor such that the flux of an electromagnetic field generated by the electromagnetic field generator will extend through the VEGF receptor; and generating an electromagnetic field burst using the electromagnetic field generator having a rate of fluctuation that activates the VEGF receptor, wherein the electromagnetic field burst has a burst period of approximately 26 msec, and wherein the rate of fluctuation is about 3831 Hertz or about 3861 Hertz.

2. The method of claim 1, wherein the VEGF receptor is part of a human bone cell.

3. The method of claim 1, wherein the VEGF receptor is part of a human vascular endothelial cell.

4. The method of claim 1, wherein VEGF receptors of a plurality of cells are activated by the electromagnetic field.

5. The method of claim 1, wherein the electromagnetic field is generated such that the electromagnetic field causes cell growth to occur that is substantially similar to cell growth that occurs when a VEGF receptor is activated by a VEGF ligand.

6. A method for activating a vascular endothelial growth factor (VEGF) receptor of one or more cells, the method comprising:

positioning an electromagnetic field generator in proximity to a VEGF receptor such that the flux of an electromagnetic field generated by the electromagnetic field generator will extend through the VEGF receptor; and generating an electromagnetic field burst using the electromagnetic field generator having a rate of fluctuation that activates the VEGF receptor, wherein the electromagnetic field burst has a burst period of approximately 5.5 msec, and wherein the rate of fluctuation is about 3831 Hertz or about 3861 Hertz.

7. The method of claim 6, wherein the VEGF receptor is part of a human bone cell.

8. The method of claim 6, wherein the VEGF receptor is part of a human vascular endothelial cell.

9. The method of claim 6, wherein VEGF receptors of a plurality of cells are activated by the electromagnetic field.

10. The method of claim 6, wherein the electromagnetic field is generated such that the electromagnetic field causes cell growth to occur that is substantially similar to cell growth that occurs when a VEGF receptor is activated by a VEGF ligand.

11. A method for activating a vascular endothelial growth factor (VEGF) receptor of one or more cells, the method comprising:

positioning an electromagnetic field generator in proximity to a VEGF receptor such that the flux of an electromagnetic field generated by the electromagnetic field generator will extend through the VEGF receptor; and generating an electromagnetic field burst using the electromagnetic field generator having a rate of fluctuation that activates the VEGF receptor, wherein the electromagnetic field burst has a burst period of approximately 26 msec, and wherein the rate of fluctuation is about 62 kHz to 63 kHz.

\* \* \* \* \*